(12) United States Patent
Zreiqat et al.

(10) Patent No.: US 8,765,163 B2
(45) Date of Patent: Jul. 1, 2014

(54) BIOCOMPATIBLE MATERIAL AND USES THEREOF

(75) Inventors: Hala Zreiqat, Chatswood (AU); Chengtie Wu, Kelvin Grove (AU); Colin Dunstan, Beecroft (AU)

(73) Assignee: The University of Sydney, New South Wales (AU)

( * ) Notice: Subject to any disclaimer, the term of this patent is extended or adjusted under 35 U.S.C. 154(b) by 542 days.

(21) Appl. No.: 13/003,462

(22) PCT Filed: Jul. 10, 2009

(86) PCT No.: PCT/AU2009/000892
§ 371 (c)(1),
(2), (4) Date: Jan. 10, 2011

(87) PCT Pub. No.: WO2010/003191
PCT Pub. Date: Jan. 14, 2010

(65) Prior Publication Data
US 2011/0111005 A1 May 12, 2011

(30) Foreign Application Priority Data
Jul. 10, 2008 (AU) ................................ 2008903557

(51) Int. Cl.
*A61K 33/30* (2006.01)
*C01B 33/24* (2006.01)
*C04B 35/22* (2006.01)

(52) U.S. Cl.
USPC ............ 424/423; 424/641; 501/154; 423/331

(58) Field of Classification Search
USPC .................... 424/423, 641; 501/154; 423/331
See application file for complete search history.

(56) References Cited

U.S. PATENT DOCUMENTS

2007/0248575 A1* 10/2007 Connor et al. ............... 424/93.7

FOREIGN PATENT DOCUMENTS

| WO | WO 2007/020613 A1 | 2/2007 |
| WO | WO 2008/104964 A2 | 9/2008 |

OTHER PUBLICATIONS

Boyd, et al., "The role of $Sr^{2+}$ on the structure and reactivity of $SrO$—$CaO$—$ZnO$—$SiO_2$ ionomer glasses", J. Mater. Sci.: Mater Med, 2008, Published Aug. 1, 2007, vol. 19, pp. 953-957.
Boyd, et al., "Preliminary investigation of novel bone graft substitutes based on strontium—calcium—zinc—silicate glass", J. Mater, Sci.: Mater Med. 2009, Published online: Oct. 7, 2008, vol. 20, pp. 413-420.
Clarkin, et al. "Comparison of an experimental bone cement with a commercial control, Hydroset™", J. Mater, Sci.: Mater, Med, 2009, Published online: Feb. 13, 2009, vol. 20, pp. 1563-1570.

(Continued)

*Primary Examiner* — Lezah Roberts
*Assistant Examiner* — Tracy Liu
(74) *Attorney, Agent, or Firm* — Nixon Peabody LLP; Jeffrey L. Costellia

(57) ABSTRACT

The present invention relates to a biocompatible ceramic material comprising Sr, Mg or Ba doped Hardystonite ($Ca_2ZnSi_2O_7$), and a method for its synthetic preparation. The present invention also relates to an implantable medical device comprising biocompatible doped Hardystonite, and a method for its production. The present invention further relates to a method for improving the long term stability of an implantable medical device and an implantable drug delivery device comprising doped Hardystonite. Further, the present invention relates to the use of comprising biocompatible doped Hardystonite in the regeneration or resurfacing of tissue.

10 Claims, 14 Drawing Sheets

(56) References Cited

OTHER PUBLICATIONS

Clarkin, et al. "Comparison of failure mechanisms for cements used in skeletal luting applications", J. Mater, Sci.: Mater, Med. 2009, Published online: Mar. 13, 2009, vol. 20, pp. 1585-1594.

Wu, et al. "The Effect of Zn Contents on Phase Composition, Chemical Stability and Cellular Bioactivity in Zn—Ca—Si System Ceramics", J. Biomedical Materials Research Part B:, Applied Biomaterials, May 7, 2008. vol. 87, No. 2, pp. 346-353.

Kakitani, et al., "Synthesis of Solid Solutions Based on the Akermanite and/or Hardystnite Systems and Their Fluorescence Properties", Jpn J. Appl. Phys., Nov. 1997, vol. 36, Part 1, No. 11, pp. 6793-6797.

International Search Report for PCT/AU2009/000892 dated Aug. 7, 2009.

* cited by examiner

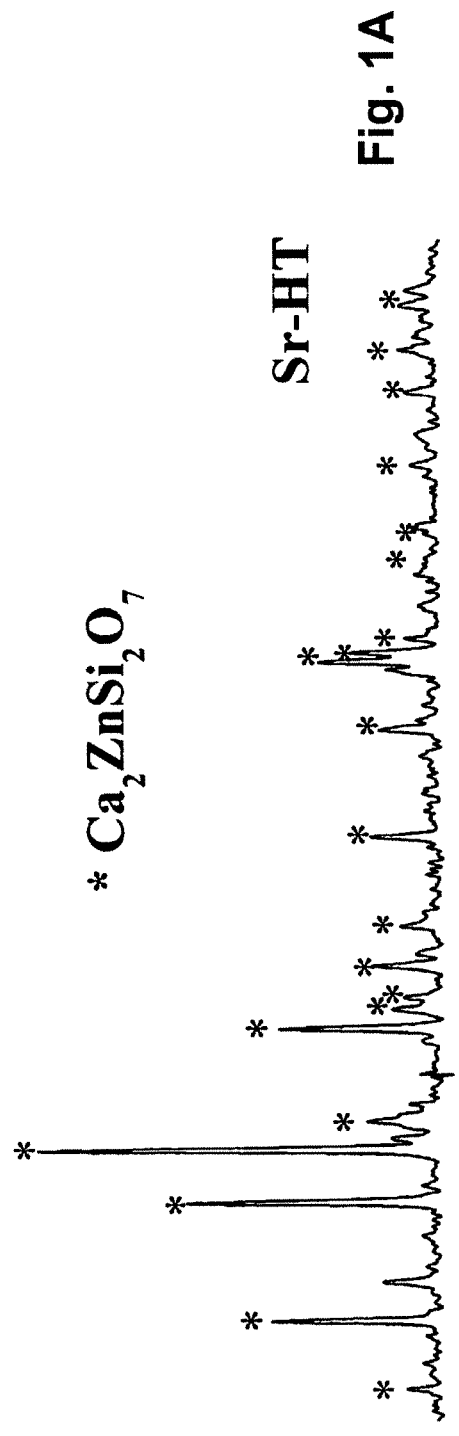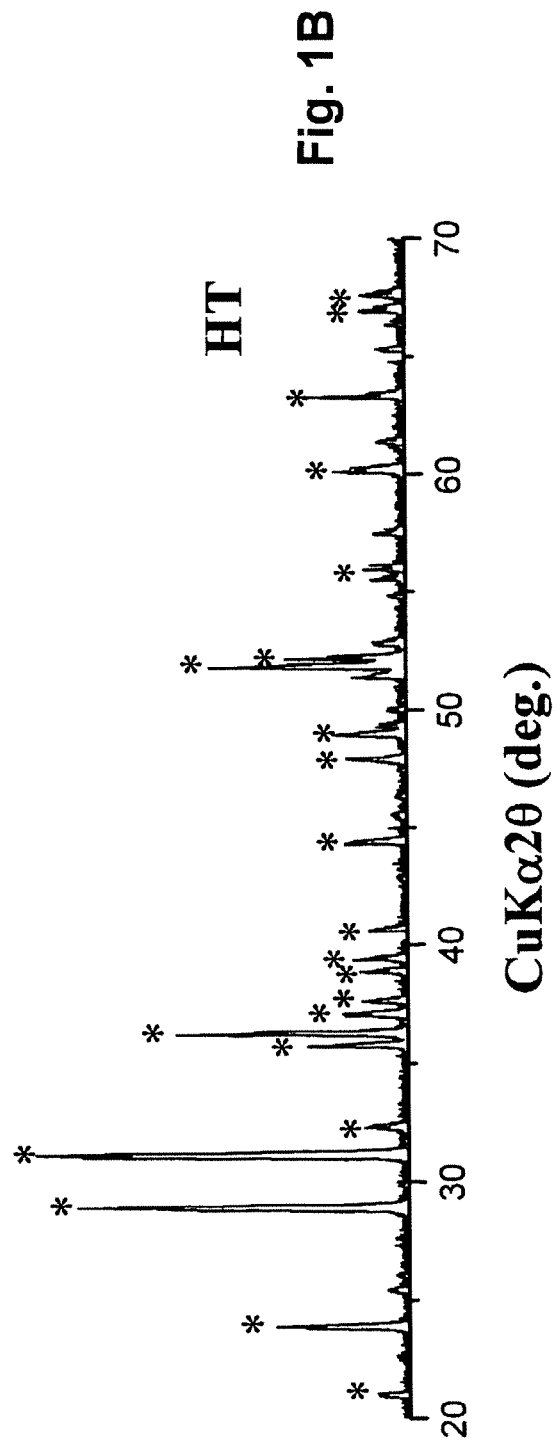

| Scaffolds | Porosity (%) | Compressive Strength (MPa) |
|---|---|---|
| Spongy bone | 70-90 | 0.2-4.0 |
| Hydroxyapatite | 69-86 | 0.03-0.29 |
| CaSiO$_3$ | 82 | 0.32 |
| Sr-HT | 78 | 2.16 |

Fig. 2

BIOCOMPATIBLE MATERIAL AND USES THEREOF

FIELD OF THE INVENTION

The present invention relates to a biocompatible material and in particular to a biocompatible calcium zinc silicate based material. In one embodiment the invention has been developed for use in tissue regeneration including bone tissue. In other embodiments the invention has been developed as a coating to improve the long-term stability of prior art implantable medical devices. In another embodiment the invention has been developed for use in drug delivery or for skeletal tissue regeneration. However, it will be appreciated that the invention is not limited to these particular fields of use.

BACKGROUND OF THE INVENTION

The following discussion of the prior art is provided to place the invention in an appropriate technical context and enable the advantages of it to be more fully understood. It should be appreciated, however, that any discussion of the prior art throughout the specification should not be considered as an express or implied admission that such prior art is widely known or forms part of common general knowledge in the field.

Bone, as a living tissue, has the ability to heal itself, however in some cases damage to the bone from whatever cause is too severe to allow natural healing to take place, and so a bone graft is required to stimulate regeneration. There are three main types of bone grafts: autografts, allografts and synthetic grafts. Significant research is being conducted in the field of synthetic grafts as bone substitutes since synthetic grafts can ameliorate many of the problems associated with autografts and allografts, such as limited supply, donor site pain, and immunogenicity issues.

In the case of advanced degenerative bone disease, joint replacement therapy remains the only treatment available for relieving the pain and suffering. However, the technologies available in this area of orthopaedics are far from satisfactory. For example, Australians require more than 60,000 hip and knee replacement operations annually, a rate that has been estimated to be increasing by some 10% per annum, and a staggering 25% of which are revisions of failed implants [Graves, S. E., et al., The Australian Orthopaedic Association National Joint Replacement Registry. *Med. J Aust.*, 2004; 180 (5 Suppl): p. S31-4]. Further complications arise in situations where bone stock is compromised, or where initial implant stability is questionable (e.g. elderly patients, post-traumatic injuries or in revision operations), in which cases short- and long-terms clinical results are typically inferior. The increases in life expectancy, and in the number of younger patients requiring implants, highlights the need for greater implant longevity and has driven biomedical research to develop novel micro-engineered surfaces to anchor the cementless prosthesis directly to the living bone through osseo-integration, thereby attempting to provide a stable interface strong enough to support life-long functional loading. It is clear that there is a serious problem with the longevity of current orthopaedic devices; a problem that is anticipated to only increase with the increasing demand from the aging population requiring such treatments. It is clear that any improvement that could be made to increase the performance of these orthopaedics devices would be welcomed, not only by the orthopaedic community but also by the patients themselves.

3D scaffolds that promote the migration, proliferation and differentiation of bone and endothelial cells are becoming increasingly important in not only orthopaedic but also maxillofacial surgery. An ideal bone replacement material should support bone formation and vascularisation; show minimal fibrotic reaction and serve as a temporary biomaterial for bone remodelling; they must degrade in a controlled fashion into non-toxic products that the body can metabolize or excrete via normal physiological mechanisms (Yaszemski et al. 1996). Scaffolds need to be mechanically strong and matched with a similar modulus of elasticity to that of bone in order to prevent stress shielding as well as maintaining adequate toughness to prevent fatigue fracture under cyclic loading. At present there are no successful strategies available for bone tissue regeneration and resurfacing arthritic joints with articular cartilage. The lack or of cartilage reparative response creates a great demand for new modalities that promote tissue regeneration.

Over the last century, various ceramics have been investigated for the purpose of encouraging or stimulating bone growth and as scaffolds. For example, in the 1880's calcium sulphate (plaster of Paris) was utilised, however calcium sulphate displays a relatively low bioactivity and a relatively high rate of degradation (Tay et al., *Orthop. Clin. North Am.*, 1999, 30:615-23). In the 1950's hydroxyapatite was utilised, however hydroxyapatite suffers from a relatively low degradation rate and poor mechanical properties (Wiltfang J., et al *J. Biomed. Mater. Res.* 2002; 63:115-21). In the 1970's Bioglass® was developed, however, this material is relatively hard to handle due to its inherent brittleness and has a relatively low bending strength (Cordioli G, *Clin. Oral Implants Res.* 2001, 13:655-65). In the 1990's calcium silicate ceramics began to be used for stimulating bone growth. They are regarded as potential bioactive materials and their degradation products do not incite an inflammatory reaction. However drawbacks exist with these materials that compromise their physical and biological properties including their a) inability to combine the required mechanical properties with open porosity b) poor mechanical strength making them unsuitable for load-bearing application; and c) poor chemical instability (high degradation rate) leading to a highly alkaline condition in the surrounding environment which is detrimental to cell viability and limits their long-term biological applications.

Whilst other more recent ceramics such as HAp, Bioverit®, Ceraverit® and other calcium silicates have been found to bond to living bone and meet wide clinical applications, i.e. good bioactivity, they cannot be used in highly loaded areas, such as the cortical bone found in, for example, legs, due to the relative brittleness of these materials. Thus the materials possess good bioactivity, but lack full biodegradability after implantation and their mechanical strength is compromised [Hench L L. *J Am Ceram. Soc.* 1998 81: 1705-28]. They are too brittle and fracture frequently. For at least this reason such materials typically find their use limited to coatings on metallic implants.

It is an object of the present invention to overcome or ameliorate at least one of the disadvantages of the above mentioned prior art, or to provide a useful alternative.

SUMMARY OF THE INVENTION

According to a first aspect, the present invention provides a biocompatible ceramic material having a molecular formula:

$$[(Sr_aBa_bMg_c)Ca_{[2.0-\Sigma(a,b,c)]}ZnSi_2O_7]$$

wherein $\Sigma(a,b,c)$ is between 0.05 to 0.9.

According to a second aspect, the present invention provides for a calcium zinc silicate doped with an element selected from the group consisting of Sr, Mg, Ba or combinations thereof.

Preferably the dopant, namely the Sr, Mg, Ba or combinations thereof, at least partially substitutes the calcium in said calcium zinc silicate. In other preferred embodiments, wherein the dopant is Sr, the molecular formula of the Sr-calcium zinc silicate is $Sr_xCa_{(2-x)}ZnSi_2O_7$, wherein x is between 0.05 to 0.9. Preferably x=0.1.

In one preferred embodiment the calcium is at least partially substituted with Mg, or may be completely replaced by Mg.

According to a third aspect, the present invention provides for strontium calcium zinc silicate ($Sr_{0.1}Ca_{1.9}ZnSi_2O_7$).

According to a fourth aspect, the invention provides for a biocompatible material comprising strontium calcium zinc silicate. In one preferred embodiment the strontium calcium zinc silicate is strontium doped Hardystonite ($Ca_2ZnSi_2O_7$).

The skilled person will appreciate the term "biocompatible" defining a two-way response, i.e. the body's response to the material and the materials response to the body's environment. The biocompatibility of a medical device refers to the ability of the device to perform its intended function, with the desired degree of incorporation in the host, without eliciting any undesirable local or systemic effects in that host.

In preferred embodiments the biocompatible material of the invention is a medical grade or an implant grade material. In one embodiment, the biocompatible material is essentially "pure", comprising a purity of greater than about 95%, and more preferably greater than about 99%. Preferably the purity is greater than about 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99%. Desirably the strontium calcium zinc silicate material comprises a transmission X-ray diffraction pattern having the following diffraction angles 2θ with three strongest characteristic peaks:

lines of strong intensity: 31.44 degrees,
lines of medium intensity: 29.225 degrees, and
line of third strongest intensity: 36.565 degrees.

Preferably the strontium calcium zinc silicate material of one embodiment of the invention comprises a transmission X-ray diffraction pattern as per FIG. 1A.

Preferably the strontium doped calcium zinc silicate has a biocompatibility when placed in physiological fluid. Preferably the biocompatible material of the invention forms a hydroxyapatite layer upon exposure to bodily fluids. As the skilled person will appreciate, the formation of hydroxyapatite is widely recognised as strong evidence that the body accepts the material as sui generis and is a requirement for the implant to chemically bond with living bone.

Whilst in preferred embodiments the biocompatible strontium calcium zinc silicate material of the invention is pure, in other embodiments the material includes impurities, which may be in significant quantities. However, if impurities are present the impurities themselves are preferably biocompatible and/or do not result in any significant degradation of biocompatibility for the overall material. In other words, as the skilled person will appreciate, some tolerance to impurities may be acceptable. In one aspect, the biocompatible material of the invention is a strontium calcium zinc silicate compound with little or no impurity.

Preferably the Sr:Ca ratio is between about 0.025 to 0.85. For example the Sr:Ca ratio may have a value of 0.025, 0.05, 0.075, 0.1, 0.125, 0.15, 0.175, 0.2, 0.225, 0.25, 0.275, 0.3, 0.325, 0.35, 0.375, 0.4, 0.425, 0.45, 0.475, 0.5, 0.525, 0.55, 0.575, 0.6, 0.625, 0.65, 0.675, 0.7, 0.725, 0.75, 0.775, 0.8, or 0.825.

Preferably the molecular formula of the Sr-calcium zinc silicate is $Sr_xCa_{(2-x)}ZnSi_2O_7$, wherein x lies between 0.05 to 0.9. Preferably x=0.1. Preferably x is 0.5, 0.55, 0.6, 0.65, 0.7, 0.75, 0.8, 0.85, or 0.9. It will be appreciated that the Sr dopant may alternatively be Mg or Ba. The dopant may also be a mixture of Sr, Mg, or Ba.

In some embodiments the strontium may be substantially substituted with a variant, which may be selected from the group consisting of Mg and Ba.

Zinc is reported to be involved in bone metabolism, stimulate bone formation and increase bone protein, calcium content and alkaline phosphotase activity in humans and animals.

Hardystonite ($Ca_2ZnSi_2O_7$) is a mineral containing zinc, calcium and silicon with a melting temperature of 1425° C. and a density of 3.4 g/cm$^3$. The present applicants have shown that incorporation of zinc in calcium silicates (i.e. $CaSiO_3$) by a sol-gel method modified its physical and biological properties, resulting in the formation of a pure material known as Hardystonite i.e. $Ca_2ZnSi_2O_7$ (Wu C., Chang J., and Zhai W., *Ceram. International* 31 (2005) 27-31). The study concluded that Hardystonite could be obtained by the sol-gel method and showed improved bending and fracture toughness as compared to hydroxyapatite. Preliminary studies indicated that the Hardystonite could possess biocompatibility.

The applicant's studies on incorporating strontium into $CaSiO_3$ bioactive ceramics showed that strontium modified calcium silicates (Sr—$CaSiO_3$) was a new and potential bioactive material (Wu C., Ramaswamy Y., Kwik D. and Zreiqat H., *Biomaterials* 28 (2007) 3171-3181).

In the present invention, a novel material, strontium calcium zinc silicate ($Sr_{0.1}Ca_{1.9}ZnSi_2O_7$) was obtained by combining Zn and Sr ions in the Ca—Si system by partly replacing Ca ions in Hardsytonite with Sr by a sol-gel method. The new material showed surprisingly enhanced biological properties which were unexpectedly better than that of related known materials. The present disclosure is the first time that the strontium calcium zinc silicate material of the invention has been synthetically prepared and its potential use as a biocompatible material explored. The present Applicants have discovered that, surprisingly, strontium calcium zinc silicate displays exceptional biocompatibility, and more particularly, is particularly suited for the regeneration of bone and other tissue. In one embodiment, the biocompatible strontium calcium zinc silicate finds particular utility in resurfacing arthritic joints to promote the growth of articular cartilage. In other embodiments, the biocompatible material of the invention is useful in the development of 3D scaffolds which promote migration, proliferation and differentiation of bone and endothelial cells, for example in orthopaedic and maxillofacial surgeries, and yet provides sufficient mechanical properties for load-bearing parts. The strontium calcium zinc silicate material supports bone tissue regeneration/formation and vascularization and yet also provides minimal fibrotic reactions. In one aspect, the present invention provides biphasic scaffolds for osteochondral defects. In yet other embodiments, the present invention provides a strontium calcium zinc silicate which is coatable on currently used orthopaedic and dental implants to provide enhanced long-term implant stability. The strontium calcium zinc silicate is also useful as coatings for skeletal tissue regeneration.

As discussed previously, the development of bioglass, glass-ceramics, and bioceramics containing CaO and $SiO_2$ for bone tissue regeneration has received great attention in the past 3 decades. The stimulatory effect of the Ca and Si containing ionic products released from materials on osteoblast proliferation, differentiation, and related gene expression, and mineralization have also been well documented (see for example Xynos I. D., et al in *Ionic products of bioactive glass dissolution increase proliferation of human osteoblasts and induce insulin-like growth factor II mRNA expression and protein synthesis, Biochem. Biophy. Res. Commun.* 2000; 276:461-465). $CaSiO_3$ based materials are considered as potential bioactive materials for bone tissue regeneration and implant coatings due to their bioactivity. However, a major drawback of the $CaSiO_3$ ceramics is their relatively high dissolution rate leading to a high alkaline pH value in the surrounding environment, (see for example Siriphannon P., et al in *Formation of hydroxyapatite on $CaSiO_3$ powders in simulated body fluid, J. Eur. Ceram. Soc.* 2002; 22:511-520). Indeed, the bonding of $CaSiO_3$ coatings to titanium substrate degrades with the increasing immersion time in simulated body fluid (SBF) due to the relatively fast dissolution rate of the coating, which limits further biological applications. The present applicants have unexpectedly found that the chemical modification of calcium silicate with the elements zinc and strontium to produce a strontium calcium zinc silicate provides a bioceramic with significantly improved properties compared to previously known calcium silicates and previously known bioceramic materials. It appears that the presence of zinc and strontium provides a hitherto unexpected synergy with regard to the properties of the material and biocompatibility. In particular, the biocompatible strontium calcium zinc silicate of the present invention provides many of the advantages of the $CaSiO_3$ materials but ameliorates many of its disadvantages. The strontium calcium zinc silicate displays a relatively reduced dissolution profile, which is associated with a relatively reduced pH compared to $CaSiO_3$ materials. Further the densification of the calcium silicate is stimulated and the ability of apatite formation is maintained. It is also likely that Human Bone Derived Cell proliferation is stimulated.

Further, strontium calcium zinc silicate exhibits excellent mechanical properties like bending strength and fracture toughness. It also allows attachment and proliferation of bone cells. In particular, the strontium calcium zinc silicate of the invention has been found to form a chemical bond with bone, and the ability to form an apatite layer. Furthermore strontium calcium zinc silicate, displays relatively reduced corrosion as compared with $CaSiO_3$.

According to a fifth aspect, the present invention provides a method for the preparation of a biocompatible material, comprising the steps of: providing a sol of precursor materials for producing a calcium zinc silicate doped with an element selected from the group consisting of Sr, Mg, Ba or combinations thereof, at least partially gelling the sol, and drying and sintering said at least partially gelled sol to thereby form a biocompatible calcium zinc silicate doped material.

According to a sixth aspect, the present invention provides a method for the preparation of a biocompatible material, comprising the steps of: providing a sol of precursor materials for producing a Sr-doped calcium zinc silicate, at least partially gelling the sol, and drying and sintering said at least partially gelled sol to thereby form a biocompatible Sr-doped calcium zinc silicate material.

Preferably the purity of the biocompatible material produced by the method according to the fourth aspect is at least 95%, and more preferably at least 99%. Desirably the biocompatible strontium calcium zinc silicate material according to the fifth aspect comprises a transmission X-ray diffraction pattern having the following diffraction angles 2θ:

lines of strong intensity: 31.44 degrees,
lines of medium intensity: 29.225 degrees, and
line of third strongest intensity: 36.565 degrees.

The strontium doped calcium zinc silicate of the invention comprises the molecular formula $(Sr_{0.1}Ca_{1.9}ZnSi_2O_7)$, and according to the fifth and sixth aspects is sol-gel derived. However, it will be appreciated that in other embodiments any method of synthetic production of the strontium calcium zinc silicate would fall within the purview of the present invention. For example, in another embodiment, the starting materials are melted, cooled and the resulting material pulverized. The resulting powder can then be formed and hot-pressed, as is well known in the art.

According to a seventh aspect the present invention provides a biocompatible material when produced by the method according to the fifth aspect.

According to a eighth aspect the present invention provides a biocompatible strontium calcium zinc silicate when produced by the method according to the sixth aspect or a biocompatible material when produced by the method according to the fifth aspect.

According to a ninth aspect the present invention provides an implantable medical device comprising a biocompatible strontium calcium zinc silicate, or an implantable medical device comprising biocompatible calcium zinc silicate material doped with an element selected from the group consisting of Sr, Mg, Ba or combinations thereof.

The medical device is preferably is chosen from the group consisting of: a 3D implantable scaffold, an orthopaedic implant for reconstructive surgery, a dental implant/prostheses, a spine implant, implants for craniofacial reconstruction and alveolar ridge augmentation, for cartilage regeneration, an osteochondral defect implant, a surgical fastener (such as a clamp, clip, sheath, or staple), a surgical fabric, an artificial heart valve (such as a sheath, flange, leaf or hinge), a strut, a stent or a stent-graft, biphasic scaffolds for osteochondral defect, scaffolds for bone tissue regeneration and maxillofacial reconstruction that promote vascularisation and bone tissue ingrowth, coating on currently used orthodaedic and dental implants, thereby improving long-term implant stability and devices for drug delivery. However, it will be appreciated that there are many other devices which would be within the purview of the present invention. In other embodiments, the bioactive strontium calcium zinc silicate of the invention may be formed into a surgical device or as a coating on a surgical device.

A bone implant, a tooth filling, or a biocement comprising a biocompatible calcium zinc silicate material doped with an element selected from the group consisting of Sr, Mg, Ba or combinations thereof.

In one embodiment, the medical device is permanently implanted. However, in other embodiments the medical device is temporarily implanted. In some aspects the medical device is substantially biodegradable.

In one embodiment the porosity of the medical device comprising a biocompatible material is between about 20 to about 80%. However, it will be appreciated that the device could be configured to have lower or greater porosity according to the intended or desired use, and any porosity range would be within the purview of the present invention. For example porosities of 20, 25, 30, 35, 40, 45, 50, 55, 60, 65, 70, 75 or 80% are possible.

In one embodiment the pore size of the device is between about 20 to about 500 μm. However, it will be appreciated that the device could be configured to have lower or greater pore size according to the intended or desired use, and any pore size would be within the purview of the present invention. For example, pore sizes of 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, or 500 micron are possible.

Implantable devices according to the present invention have many properties that make them suitable for use as implants, including high mechanical strength, resistance to fatigue, corrosion resistance, and biocompatibility. The implants may be implanted in animals, non-limiting examples of which include reptiles, birds, and mammals, with humans being particularly preferred. Preferably the compressive strength is between about 1.8 to 5.1 MPa.

The devices of this invention may be implanted into a body in different ways, including, but not limited to subcutaneous implantation, implantation at the surface of the skin, implantation in the oral cavity, use as sutures and other surgical implantation methods.

In one embodiment, the doped calcium zinc silicate device of the present invention may be coated with at least one resorbable polymer material, non-limiting examples of which include polyglycolides, polydioxanones, polyhydroxyalkanoates, polylactides, alginates, collagens, chitosans, polyalkylene oxalate, polyanhydrides, poly(glycolide-co-trimethylene carbonate), polyesteramides, orpolydepsipeptides etc.

Alternatively, the coating material may comprise healing promoters such as thrombosis inhibitors, fibrinolytic agents, vasodilator substances, anti-inflammatory agents, cell proliferation inhibitors, and inhibitors of matrix elaboration or expression. Examples of such substances are discussed in U.S. Pat. No. 6,162,537. The present invention also contemplates using a polymer coating, (e.g. a resorbable polymer) in conjunction with a healing promoter to coat the implantable medical device.

The implantable medical device may be resorbable or completely inert towards biodegradation. When the device is resorbable, the in vivo degradation leaves behind a scaffold that reinforces the injured tissue.

According to a tenth aspect the present invention provides a method for producing an implantable medical device comprising: transferring biocompatible calcium zinc silicate onto a substrate thereby forming said implantable medical device, wherein said calcium zinc silicate is doped with an element selected from the group consisting of Sr, Mg, Ba or combinations thereof.

According to an eleventh aspect the present invention provides a method for producing an implantable medical device comprising: transferring biocompatible Sr-doped calcium zinc silicate onto a substrate thereby forming said implantable medical device. Alternatively, Mg, Ba or combinations of Sr, Mg, Ba-doped calcium zinc silicate may be transferred onto a substrate.

It will be appreciated that there are a number of methods of transferring a biocompatible doped calcium zinc silicate onto a supporting surface or substrate, and any of these methods fall within the purview of the present invention. For example, in one embodiment, where the dopant is Sr, the strontium calcium zinc silicate is plasma spray coated. As is well known in the art, this method essentially comprises the steps of spraying molten or heat softened material onto a surface to provide the coating. The material, in the form of powder, is injected into a high temperature plasma flame, where it is rapidly heated and accelerated to a high velocity. The hot material impacts on the substrate surface and rapidly cools thereby forming a coating. The coatings possess a dense structure with a thickness of about 50 μm and the bonding strength is higher than hydroxyapatite coatings.

According to a twelfth aspect the present invention provides an implantable drug delivery device comprising a calcium zinc silicate doped with an element selected from the group consisting of Sr, Mg, Ba or combinations thereof. It will be appreciated that the drug delivery device can deliver any drug and the can be shaped to suit the particular application.

According to a thirteenth aspect the present invention provides an implantable drug delivery device comprising Sr-doped calcium zinc silicate material. Alternatively the calcium zinc silicate material is doped with Sr, Mg, Ba or combinations thereof.

According to a fourteenth aspect the present invention provides an implantable medical device having a predetermined dissolution profile comprising a predetermined quantity of a calcium zinc silicate doped with an element selected from the group consisting of Sr, Mg, Ba or combinations thereof. In one preferred embodiment the dopant is Sr. For example, in one embodiment it is envisaged that the implantable drug delivery device could have a dissolution profile of Si ions as follows:

| Time (h) | Si ions released (%) |
|---|---|
| 0 | 0 |
| 24 | 0.26 |
| 72 | 0.38 |
| 168 | 0.52 |

Whilst the above dissolution profile is a single example, it will be appreciated by the skilled person that other dissolution profiles will fall within the purview of the present invention.

According to a fifteenth aspect the present invention provides a method for modifying the dissolution profile of a calcium silicate based medical device comprising: at least partially producing the device from a biocompatible strontium doped calcium zinc silicate. Alternatively the calcium zinc silicate material is doped with Sr, Mg, Ba or combinations thereof.

According to a sixteenth aspect the present invention provides a method for modifying the dissolution profile of a calcium silicate based medical device comprising: at least partially producing the device from a biocompatible calcium zinc silicate doped with an element selected from the group consisting of Sr, Mg, Ba or combinations thereof.

According to a seventeenth aspect the present invention provides a method for improving the long term stability of an implantable medical device comprising the step of: coating said device with strontium doped calcium zinc silicate. Alternatively the calcium zinc silicate material is doped with Sr, Mg, Ba or combinations thereof.

According to an eighteenth seventeenth aspect the present invention provides a method for improving the long term stability of an implantable medical device comprising the step of: coating said device with calcium zinc silicate doped with an element selected from the group consisting of Sr, Mg, Ba or combinations thereof.

Preferably the coating further includes a biocompatible polymer, which in one embodiment is PLGA. In one aspect the implantable medical device is a biphasic scaffold for an osteochondral defect.

According to a nineteenth aspect the present invention provides a use of strontium calcium zinc silicate in the regeneration or resurfacing of tissue, comprising contacting the tissue with a quantity of strontium doped calcium zinc silicate for a sufficient period to at least partially effect said regeneration or resurfacing. Alternatively the calcium zinc silicate material is doped with Sr, Mg, Ba or combinations thereof.

According to a twentieth aspect the present invention provides a use of calcium zinc silicate in the regeneration or resurfacing of tissue, comprising contacting the tissue with a quantity of calcium zinc silicate for a sufficient period to at least partially effect said regeneration or resurfacing, wherein said calcium zinc silicate is doped with an element selected from the group consisting of Sr, Mg, Ba or combinations thereof.

In one aspect, the doped calcium zinc silicate of the invention contacted with tissue includes an S100A8 or a S100A9 polypeptide, or a polynucleotide encoding S100A8 or S100A9 operably linked to a promoter, as disclosed in WO 2006/047820, which is hereby incorporated herein by reference, or any other protein that is shown to be important in bone and cartilage regeneration.

According to a twenty-first aspect the present invention provides a method for regenerating or resurfacing tissue, comprising the step of: contacting said tissue with a quantity of calcium zinc silicate doped with an element selected from the group consisting of Sr, Mg, Ba or combinations thereof.

According to a twenty-second aspect the present invention provides a method for regenerating or resurfacing tissue, comprising the step of: contacting said tissue with a quantity of Sr-doped calcium zinc silicate. Alternatively the calcium zinc silicate material is doped with Sr, Mg, Ba or combinations thereof.

According to a twenty-third aspect the present invention provides a method for forming osseous tissue on an orthopaedic defect, comprising the step of: contacting said defect with a calcium zinc silicate doped with an element selected from the group consisting of Sr, Mg, Ba or combinations thereof.

According to a twenty-fourth aspect the present invention provides a method for forming osseous tissue on an orthopaedic defect, comprising the step of: contacting said defect with a Sr-doped calcium zinc silicate. Alternatively the calcium zinc silicate material is doped with Sr, Mg, Ba or combinations thereof.

According to a twenty-fifth aspect the present invention provides a method for treating orthopaedic conditions comprising, contacting a patient in need of such treatment with an effective regenerating amount of biocompatible composition comprising calcium zinc silicate doped with an element selected from the group consisting of Sr, Mg, Ba or combinations thereof.

According to a twenty-sixth aspect the present invention provides a method for treating orthopaedic conditions comprising, contacting a patient in need of such treatment with an effective regenerating amount of biocompatible composition comprising Sr-doped calcium zinc silicate. Alternatively the calcium zinc silicate material is doped with Sr, Mg, Ba or combinations thereof.

According to a twenty-seventh aspect the present invention provides a kit for regenerating or resurfacing tissue, comprising, in a single package, a Sr-doped calcium zinc silicate and a therapeutic agent which stimulates and accelerates tissue regeneration. Alternatively the calcium zinc silicate material is doped with Sr, Mg, Ba or combinations thereof.

According to a twenty-eighth aspect the present invention provides a kit for regenerating or resurfacing tissue, comprising, in a single package, a calcium zinc silicate and a therapeutic agent which stimulates and accelerates tissue regeneration, wherein said calcium zinc silicate is doped with an element selected from the group consisting of Sr, Mg, Ba or combinations thereof.

According to a twenty-ninth aspect the present invention provides a method for the preparation of a calcium zinc silicate based biocompatible material, comprising the steps of: chemically modifying said calcium silicate based biocompatible material with an element selected from the group consisting of Sr, Mg, Ba or combinations thereof. Preferably the element is Sr.

It will be appreciated that in the foregoing ninth, tenth, eleventh, twelfth, fourteenth, sixteenth, eighteenth, twentieth, twenty-first, twenty-third, twenty-fifth, twenty-eighth or twenty-ninth aspects the biocompatible ceramic material may have a molecular formula $[(Sr_aBa_bMg_c)Ca_{[2.0-\Sigma(a,b,c)]}ZnSi_2O_7]$, wherein $\Sigma(a,b,c)$ is between 0.05 to 0.9.

The biocompatible strontium calcium zinc silicate material of the invention may be used as a fully synthetic bone graft substitute. Due to its interconnected pores, the material serves as an ideal osteoconductive scaffold and supports the formation of new host bone. As highlighted above, many of the advantages of the new material can be summarised as follows:
  Optimized porosity
  Improved mechanical strength and elasticity
  Enhanced bone ingrowth and vascularization
  Avoids potential problems common for grafting methods
  Is formable to almost any shape to suit the application
  Easy to use
  Combines with autologous bone marrow or blood
  Displays accelerated and enhanced osteointegration
The uses of the present invention are manifold, including:
  For bone void fillings or augmentation in zones requiring cancellous rather than cortical bone
  For the filling of bone defects after trauma, reconstruction, or correction in non-load or load-bearing indications
  For Trauma and orthopaedics: Filling of voids caused by cysts or osteotomies, filling of defects arising from impacted fractures, refilling of cancellous bone-harvesting sites, arthrodesis and non-unions
  For Spine surgery: Postero-lateral fusion, interbody fusion (as cage-filling material), vertebrectomies (as filling material of the vertebral implants), refilling of bone graft-harvesting sites
  For Cranio-maxillofacial surgery: Reconstruction of mandibular defects and sinus lifts

BRIEF DESCRIPTION OF THE DRAWINGS

Preferred embodiments of the invention will now be described, by way of example only, with reference to the accompanying drawings in which:

FIG. 1A an XRD analysis pattern of a calcium zinc silicate scaffold having 5% Sr ($Sr_{0.1}Ca_{1.9}ZnSi_2O_7$) ('Sr-HT'), showing that no obvious new phase is present which indicated that the incorporation of Sr into HT does not change the crystal phase, and FIG. 1B is an XRD analysis pattern of calcium zinc silicate ($Ca_2ZnSi_2O_7$) ('HT') in powder form, highlighting the peaks characteristic of the material;

FIG. 2 is a table comparing the strength of various materials, comprising spongy bone, hydroxyapatite (used clinically), $CaSiO_3$ and Sr-HT, showing that Sr-HT has high porosity, interconnectivity and mechanical strength;

FIG. 12A shows a small amount of new bone forming along the surfaces of the TCP ceramic (grey material).

FIG. 13A shows remnants of the TCP with marrow and bony fragments.

DEFINITIONS

Figure 3:
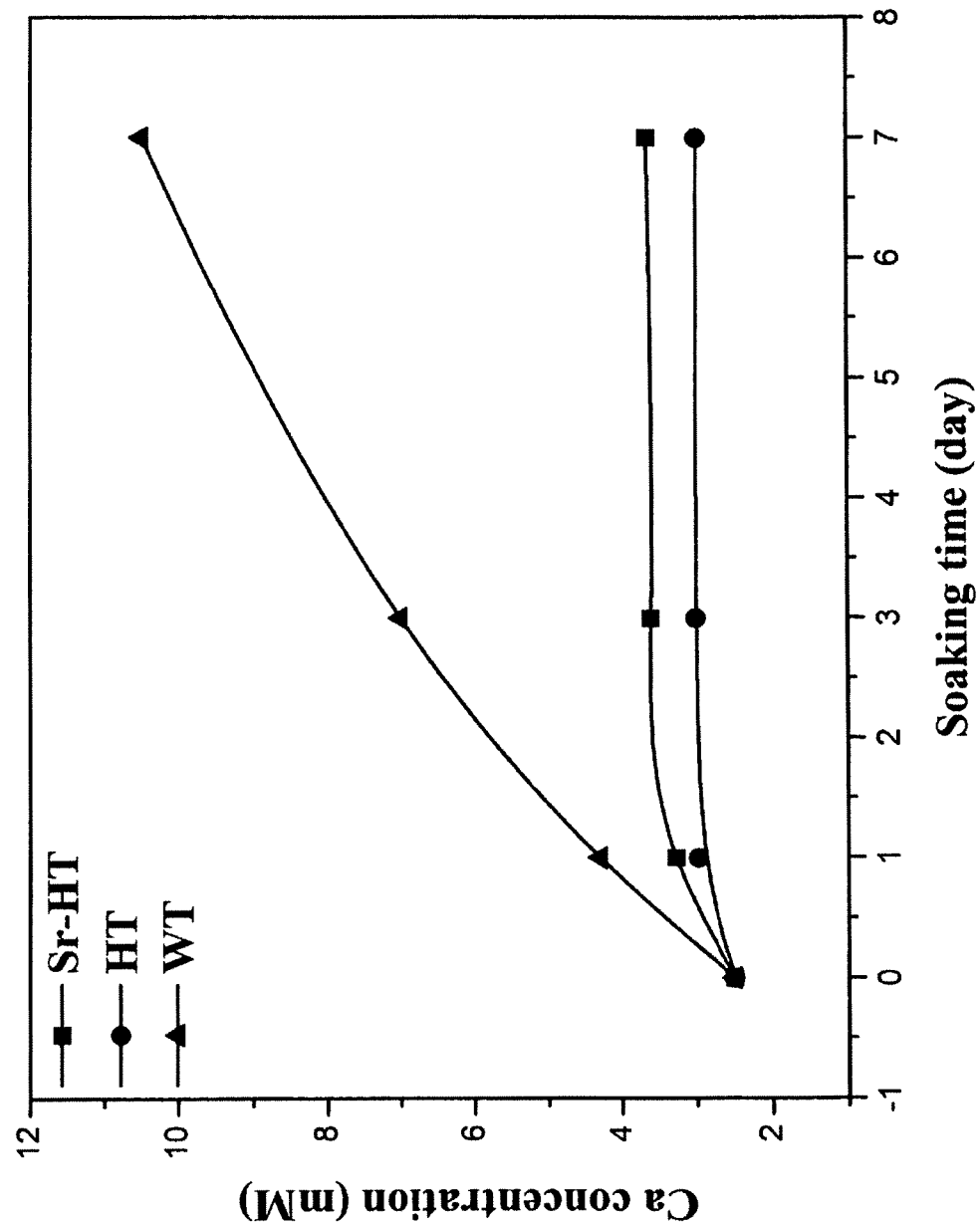
FIGS. 3 to 6 are the results of ICP-AES analyses of Ca, Si, Zn and Sr ions respectively released from ($Sr_{0.1}Ca_{1.9}ZnSi_2O_7$) (Sr-HT), $Ca_2ZnSi_2O_7$ (HT), and $CaSiO_3$ (WT) scaffolds over a 7 day period.

In describing and claiming the present invention, the following terminology will be used in accordance with the definitions set out below. It is also to be understood that the terminology used herein is for the purpose of describing particular embodiments of the invention only and is not intended to be limiting. Unless defined otherwise, all technical and scientific terms used herein have the same meaning as commonly understood by one having ordinary skill in the art to which the invention pertains.

The recitation of a numerical range using endpoints includes all numbers subsumed within that range (e.g., 1 to 5 includes 1, 1.5, 2, 2.75, 3, 3.80, 4, 5, etc.).

The terms "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

As used herein, an "implant" refers to an article or device that is placed entirely or partially into an animal, for example by a surgical procedure.

Unless the context clearly requires otherwise, throughout the description and the claims, the words 'comprise', 'comprising', and the like are to be construed in an inclusive sense as opposed to an exclusive or exhaustive sense; that is to say, in the sense of "including, but not limited to".

Other than in the operating examples, or where otherwise indicated, all numbers expressing quantities of ingredients or reaction conditions used herein are to be understood as modified in all instances by the term "about". The examples are not intended to limit the scope of the invention. In what follows, or where otherwise indicated, "%" will mean "weight %", "ratio" will mean "weight ratio" and "parts" will mean "weight parts".

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviations found in their respective testing measurements.

As used herein, 'HT' refers to calcium zinc silicate ($Ca_2ZnSi_2O_7$), and 'Sr-HT' refers to a calcium zinc silicate scaffold having Sr, e.g. $Sr_{0.1}Ca_{1.9}ZnSi_2O_7$. TCP refers to tricalcium phosphate.

PREFERRED EMBODIMENT OF THE INVENTION

Preferred embodiments of the present invention will be described in the following.

Synthesis of Hardystonite Powders

Comparative Example 1

Hardystonite powders were prepared by the sol-gel process using tetraethyl orthosilicate ($(C_2H_5O)_4Si$, TEOS), zinc nitrate hexahydrate ($Zn(NO_3)_2 \cdot 6H_2O$) and calcium nitrate tetrahydrate ($Ca(NO_3)_2 \cdot 4H_2O$) as raw materials. Briefly, the TEOS was mixed with water and 2M $HNO_3$ (mol. ratio: $TEOS/H_2O/HNO_3 = 1:8:0.16$) and hydrolysed for 30 minutes under stirring. Then the zinc nitrate hexahydrate and calcium nitrate tetrahydrate were added into the mixture (mol. Ratio: $TEOS/Zn(NO_3)_2 \cdot 6H_2O/Ca(NO_3)_2 \cdot 4H_2O = 2:1:2$) and reactants were stirred for 5 hours at room temperature. After the reaction, the solution was maintained for 60 degree centigrade for 1 day and dried at 120 degree centigrade for 2 days to obtain the dry gel. The dry gel was ground and sieved to 250 mesh, transferred into a corundum crucible and calcined at 1100 and 1200 degree centigrade for 3 hours, respectively.

The calcined powders were analysed by X-ray diffraction (XRD, Geigerflex, Rigaku Co., Japan) with a monochromated Cu K α radiation and the microstructrue of calcined powders was observed by scanning electron microscopy (SEM; JSM-6700 F, JEOL, Tokyo, Japan).

Preparation of Hardystonite Ceramics

Comparative Example 2

Figure 4:
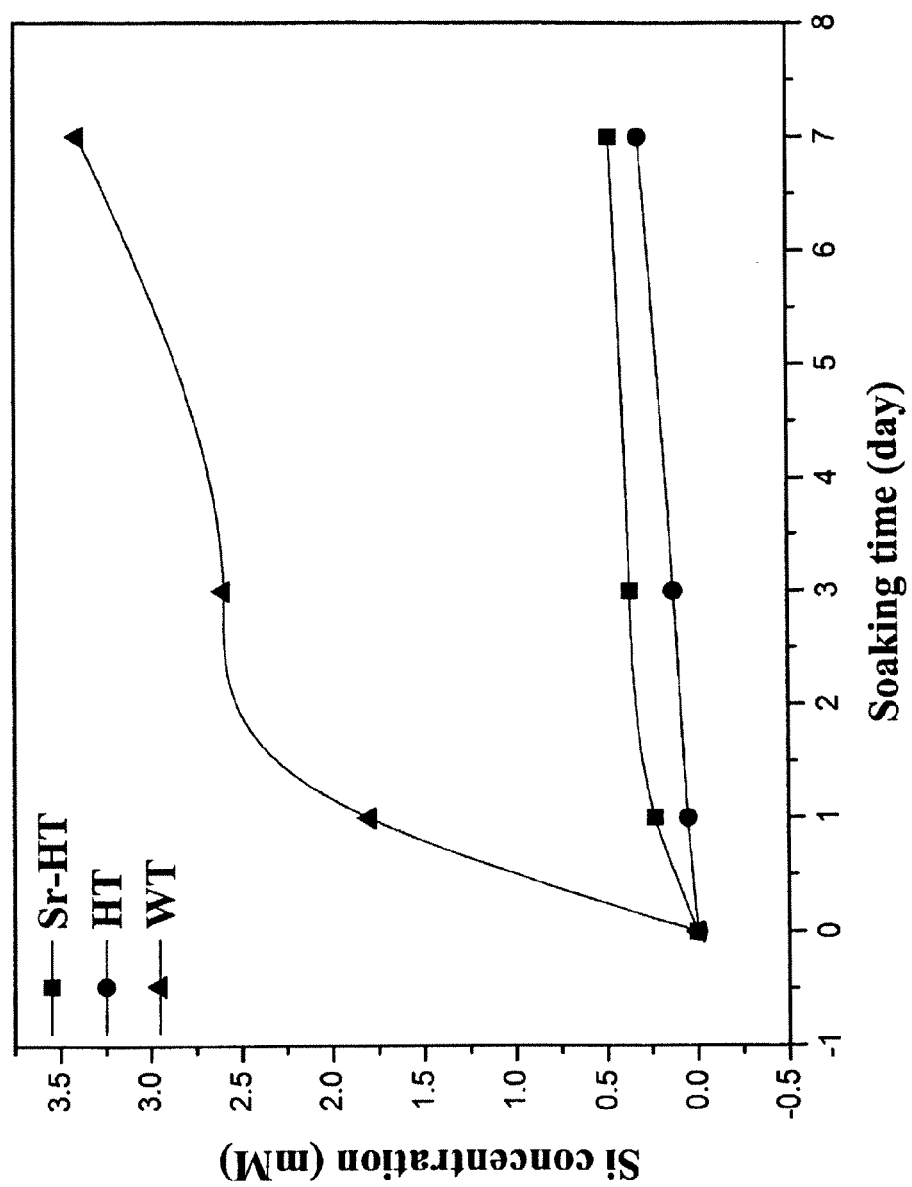
Figure 5:
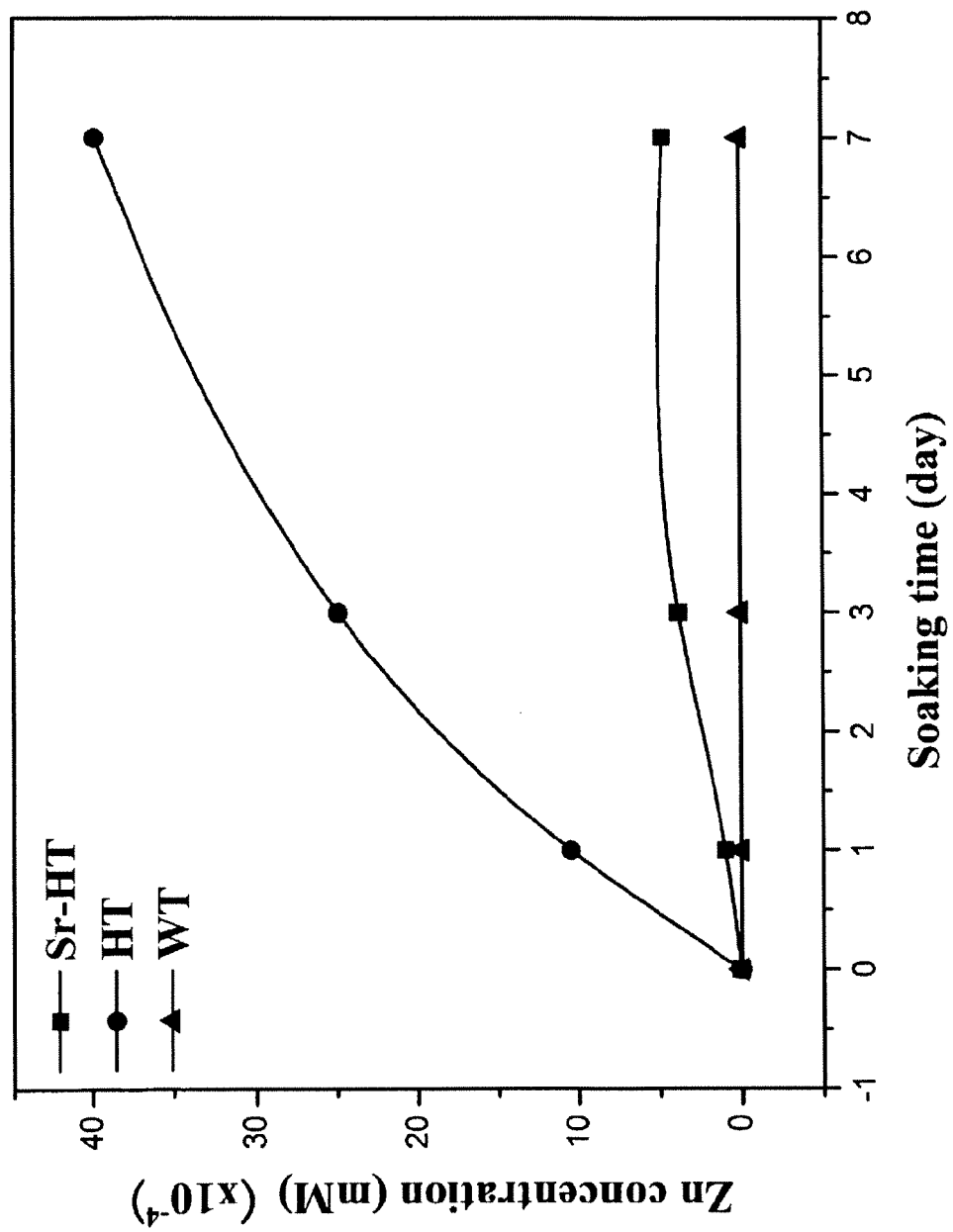
Figure 6:
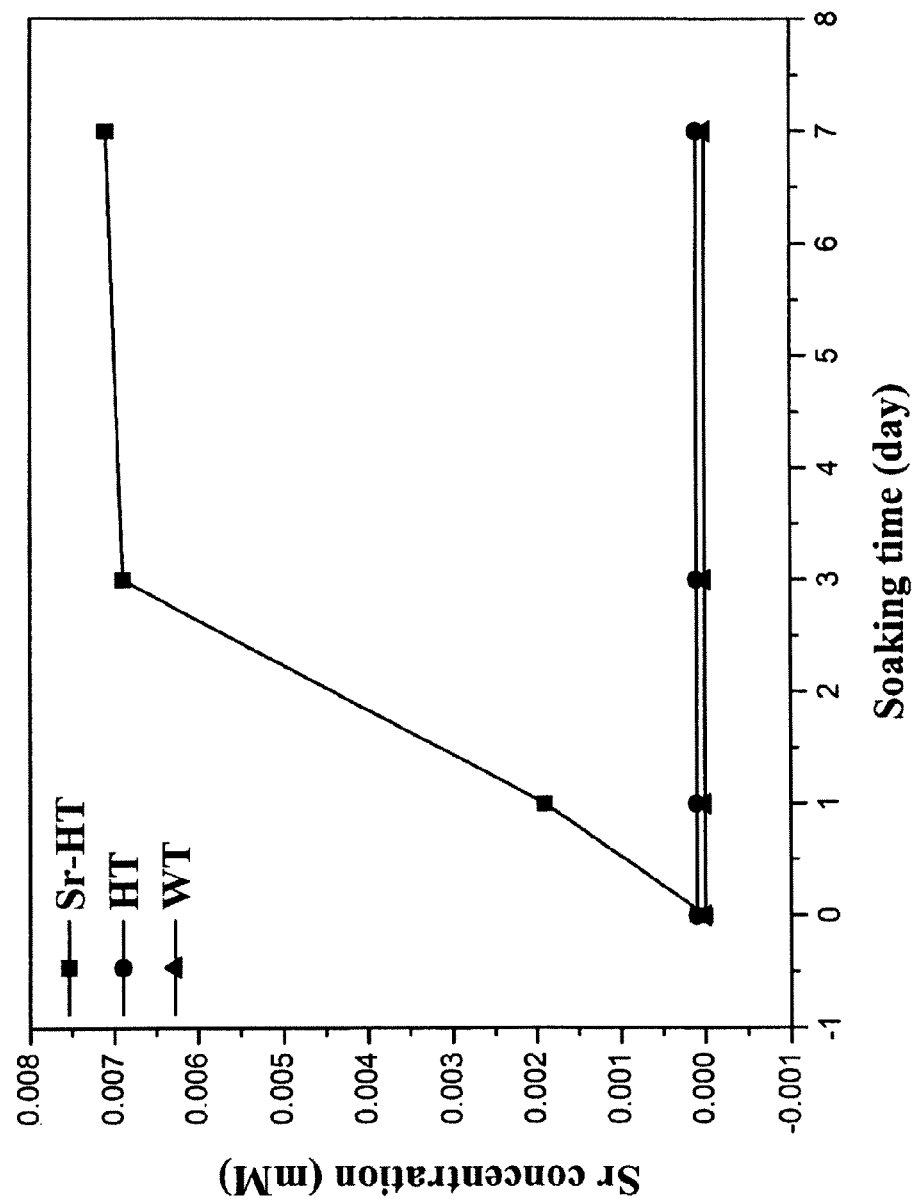

Hardystonite ceramics were prepared by uniaxial pressing of the hardystonite powders at 10 MPa followed by isostactic pressing at 200 MPa and sintered at different temperatures. To evaluate mechanical properties and sinterability, green bodies of hardystonite of 45.5 mm×8.0 mm×3.5 mm in size were prepared and fired from 1250 to 1350 degree centigrade. The sintered hardystonite ceramics were analysed by XRD and SEM. The XRD is as shown in FIG. 1. FIGS. 3 and 4 indicate that Sr—$Ca_2ZnSi_2O_7$ have a decreased Ca and Si ion dissolution profile compared with $CaSiO_3$, but has an improved dissolution compared with $Ca_2ZnSi_2O_7$. Zn and Sr ions can be released from Sr—$Ca_2ZnSi_2O_7$ but no Sr from $Ca_2ZnSi_2O_7$ and $CaSiO_3$.

Preparation and Characterisation of Sr—$CaSiO_3$ Ceramics

Comparative Example 3

Sr—$CaSiO_3$ powders containing 0, 1, 2.5, 5 and 10 mol % of Sr were synthesised by chemical precipitation method (Wu C., Zreiqat H., *Key. Eng. Mater.* 2007, 302-332, 499-502). Sr—$CaSiO_3$ powders were sieved to 230 meshes and analysed using differential thermal analysis (DTA). For the preparation of ceramic disks, Sr—$CaSiO_3$ powders were mixed with 6 wt % polyvinyl alcohol (PVA, Sigma Aldrich, USA) water solution binders (weight ratio: PVA solution/powders=1:9). The mixture was uniaxially pressed at 200 MPa to get Sr—$CaSiO_3$ green disks with a dimension of Φ15×2. Subsequently the green disks were sintered at 1100 and 1250 degree centigrade for 3 hours with a heating rate of 2 degree centigrade per minute to obtain the ceramic disks.

The sintered Sr—$CaSiO_3$ ceramic disks were analysed using X-ray diffraction (XRD, Siemens D5000, Germany) and scanning electron microscopy (SEM, Philips XL 30 CP, The Netherlands). The apparent density D of the ceramics was measured according to Archimedes Principle using the following formulation: $D=M_1/(M_2-M_3)$, where $M_1$ is the weight of the sample in air, $M_2$ the weight of sample with water and $M_3$ the weight of sample suspended in water. The relative density Rd was calculated using the formula Rd=D/Td where D is the apparent density of ceramics and Td the theoretic density of the materials.

Preparation and Characterization of Sr—$Ca_2ZnSi_2O_7$ Ceramics

Example 4

Strontium doped Hardystonite ($Sr_{0.1}Ca_{1.9}ZnSi_2O_7$) was synthesized by the sol-gel process using tetraethyl orthosilicate (($C_2H_5O)_4Si$,TEOS), zinc nitrate hexahydrate ($Zn(NO_3)_2.6H_2O$), strontium nitrate ($Sr(NO_3)_2$) and calcium nitrate tetrahydrate ($Ca(NO_3)_2.4H_2O$) as raw materials. Briefly, the TEOS was mixed with water and 2M $HNO_3$ (mol ratio: $TEOS/H_2O/HNO_3$=1:8:0.16) and hydrolyzed for 30 minutes under stirring. Then, the $Zn(NO_3)_2.6H_2O$, $Sr(NO_3)_2$ and $Ca(NO_3)_2.4H_2O$ were added into the mixture (mol ratio: $TEOS/Zn(NO_3)_2.6H_2O/Sr(NO_3)_2/Ca(NO_3)_2.4H_2O$=2:1:0.1:1.9), and reactants were stirred for 5 hours at room temperature. After the reaction, the solution was maintained at 60° C. for 1 day and dried at 100° C. for 2 days to obtain the dry gel. The dry gel was ground and transferred into a corundum crucible and calcined at 1200° C. for 3 hours, respectively.

Figure 7:
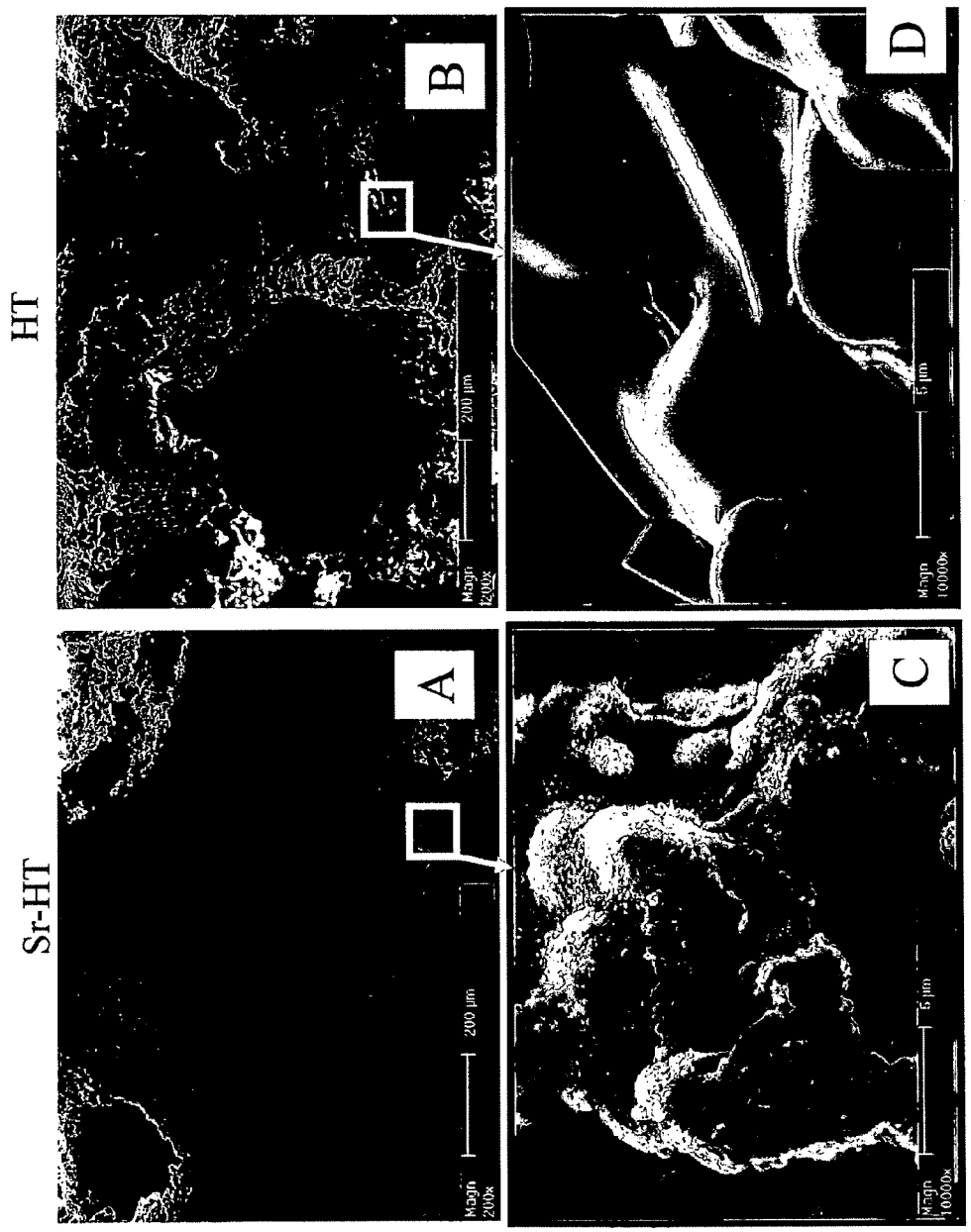
FIGS. 7A to 7D are SEM micrographs of Sr-HT and HT scaffolds soaked in SBF for 28 days, showing apatite formation on Sr-HT scaffolds (A) and (C), but no apatite formation on HT scaffolds (B) and (D)
Figure 8:
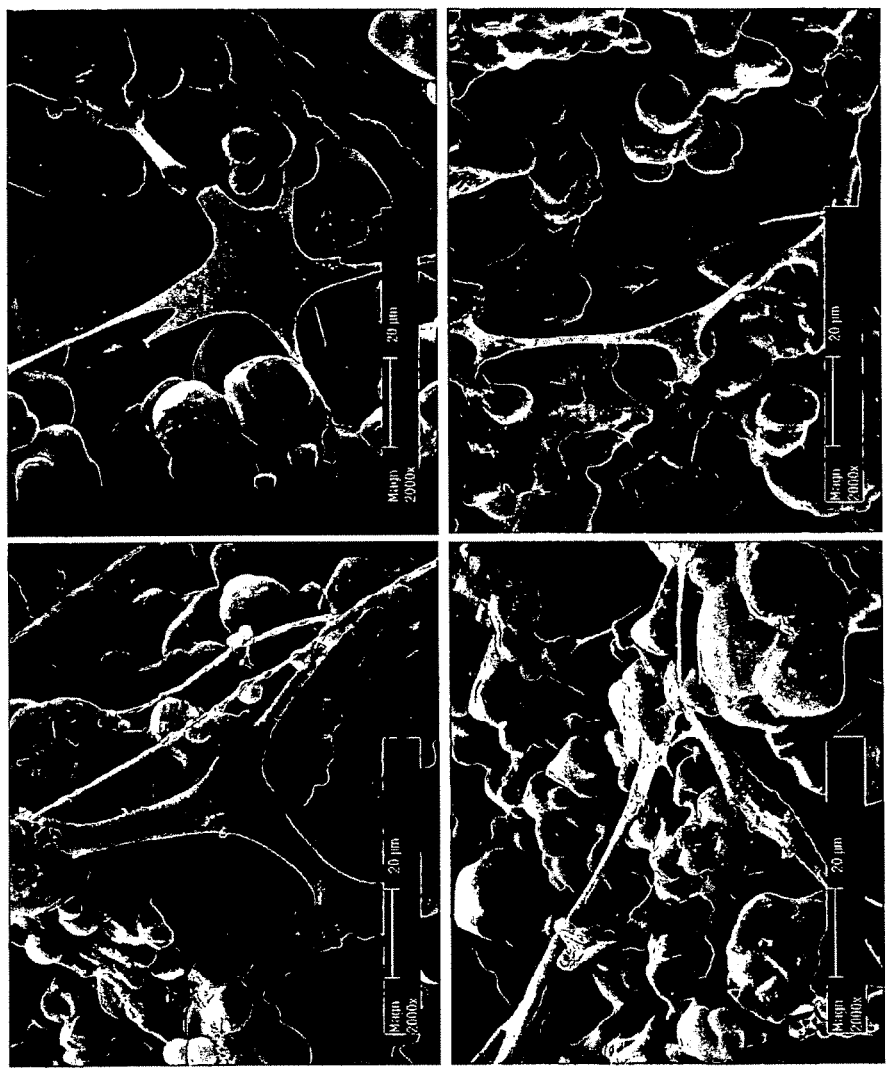
FIG. 8 shows osteoblast attachment on Sr-HT on day 3.
Figure 9:
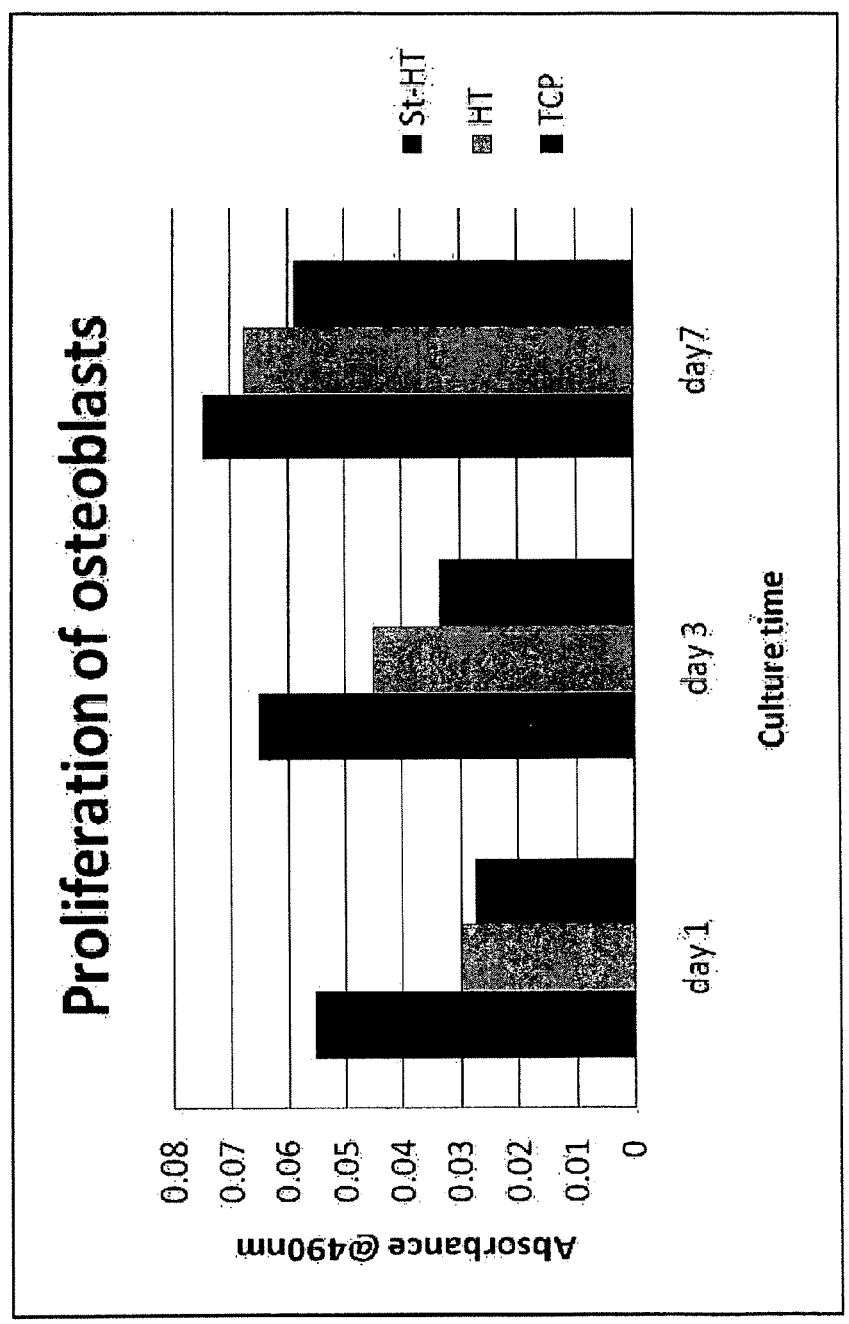
FIG. 9 shows the proliferation of osteoblasts various materials, comprising HT, Sr-HT and tricalcium phosphate.
Figure 10:
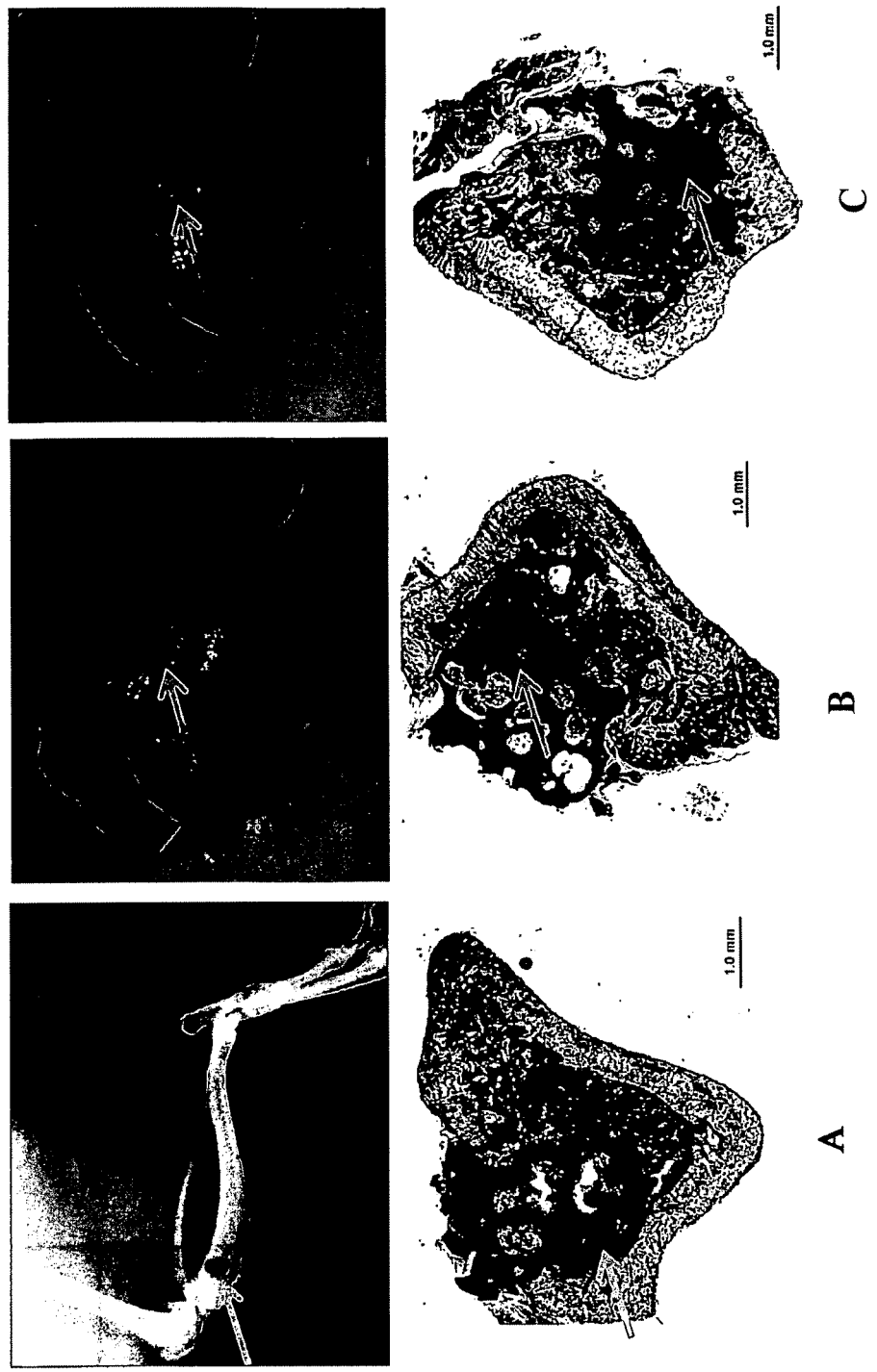
FIGS. 10A, B and C show osseointegration and resorbability of 3 dimensional scaffolds of β-TCP, HT ($Ca_2ZnSi_2O_7$), and Sr-HT (Sr—$Ca_2ZnSi_2O_7$) respectively in the cortical bone distal to the proximal tibial growth plate at 3 and 6 weeks. A hole is drilled in the rat tibia and either left vacant or filled with the scaffold. After 3 and 6 weeks the bones were removed to evaluate osseo integration. All materials were highly biocompatible with no evidence of inflammation or fibrotic reaction.
Figure 11:
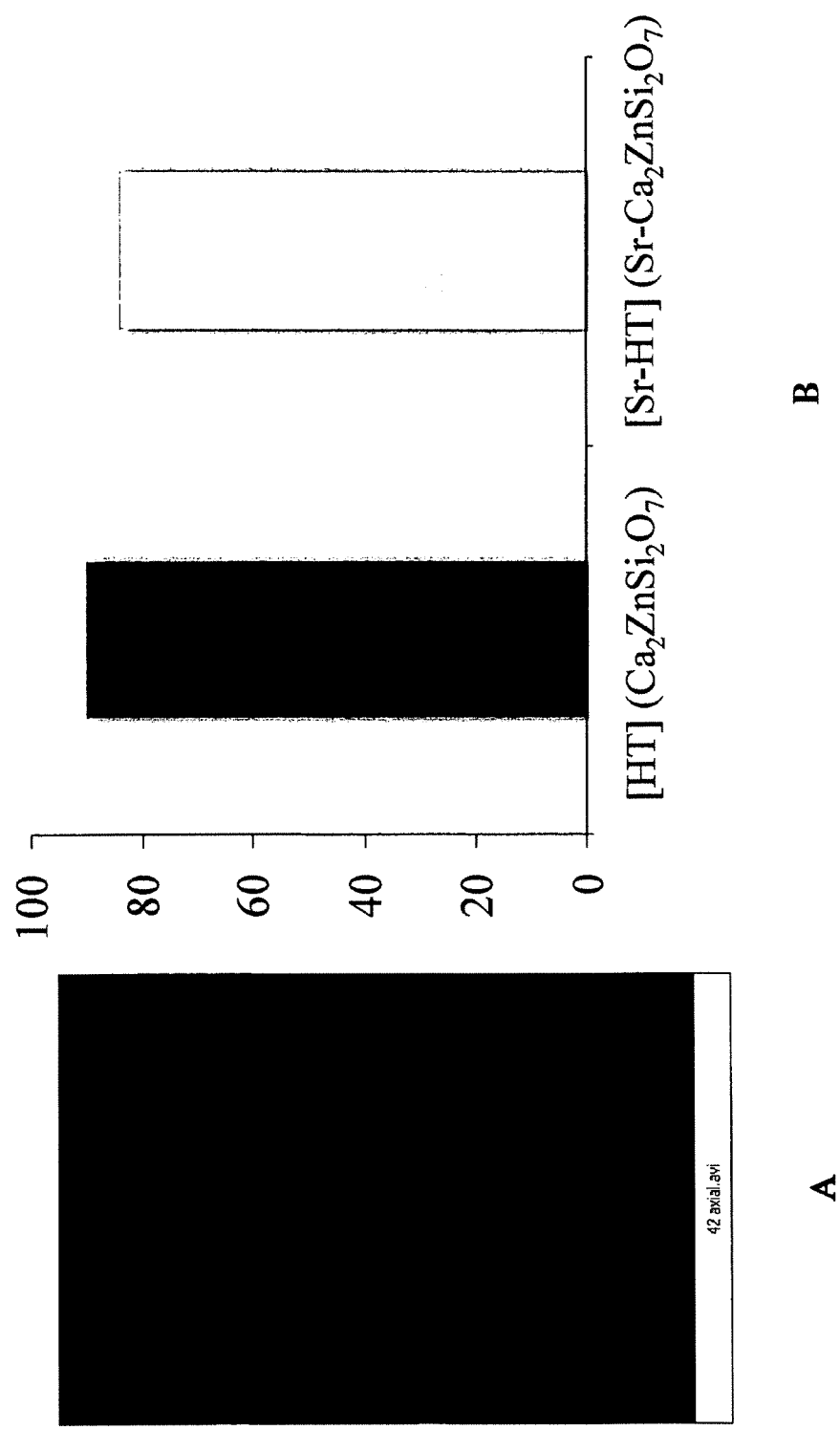
FIG. 11A shows a μ-CT analysis of the scaffolds and bone.
FIG. 11B is a graph showing the % of pore space filled with bone in the scaffolds (80% of the pores of the Sr-HT are occupied by bone)
Figure 12:
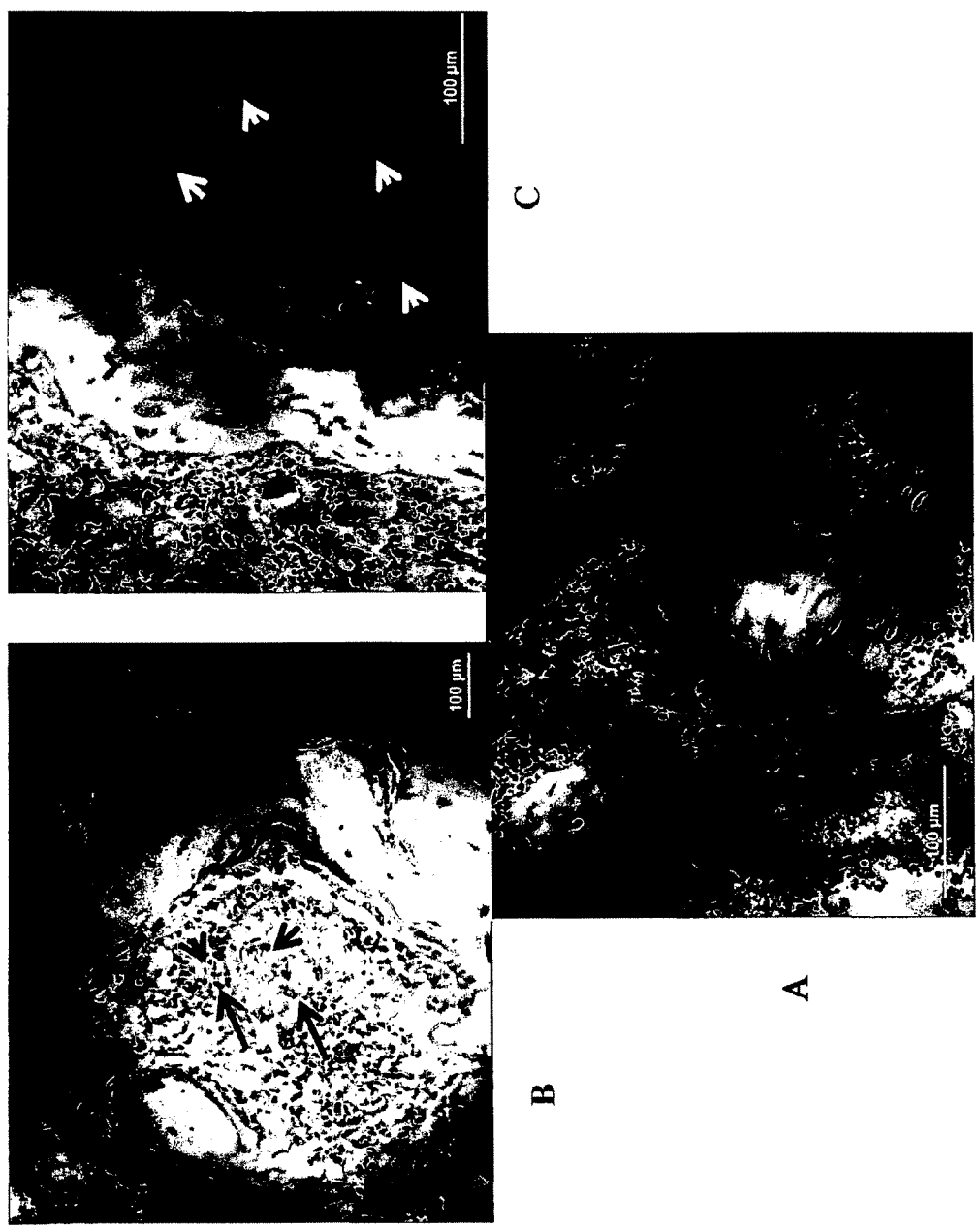
FIGS. 12A, B and C show assessment of bone formation within the implant for β-TCP, HT ($Ca_2ZnSi_2O_7$), and Sr-HT (Sr—$Ca_2ZnSi_2O_7$) respectively at 3 weeks.
FIG. 12B shows bone filling in the pores within the ceramic. The presence of OB and osteoid indicates rapid bone formation is still occurring 3 wks after implantation.
FIG. 12C shows similar bone growth within the pores to that with the HT, however it can be seen that the ceramic is breaking down with infiltration of the bone matrix through the ceramic structure, which indicates that this material is more degradable compared to the relatively stable material (HT), and supports bone formation.
Figure 13:
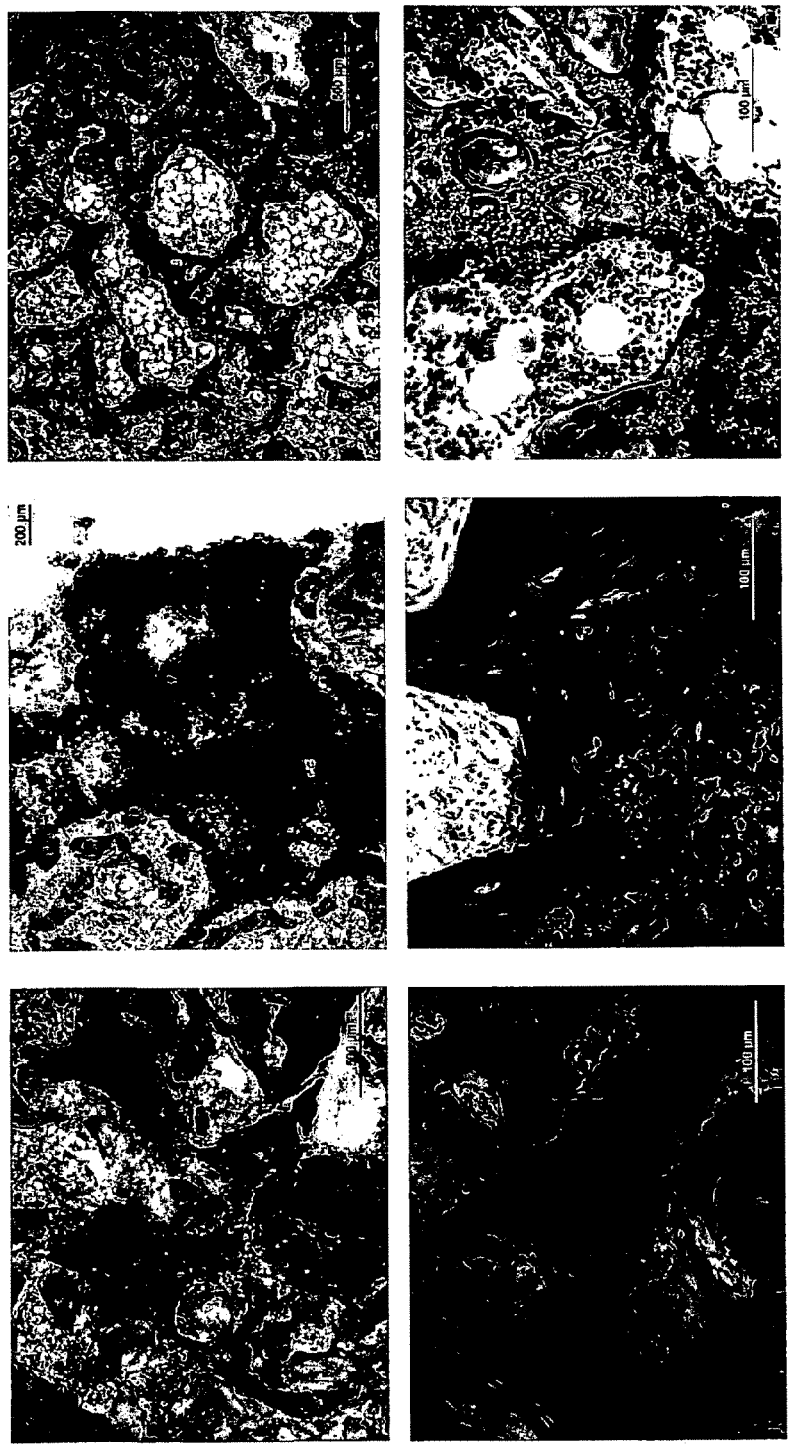
FIGS. 13A, B and C show assessment of bone formation within the implant for β-TCP, HT ($Ca_2ZnSi_2O_7$), and Sr-HT (Sr—$Ca_2ZnSi_2O_7$) respectively at 6 weeks. These figures show that there is ongoing break down of the ceramic and replacement with bone.
FIG. 13B shows that the HT material is more stable with bone filling the pores around the remaining ceramic and the ceramic structure being substantially maintained.
FIG. 13C shows some bone in the pores, however at higher magnification it can be seen that the ceramic structure is breaking down and becoming infiltrated with bone matrix. There is more rapid break down of the ceramic compared to HT.

Strontium doped Hardystonite ($Sr_{0.1}Ca_{1.9}ZnSi_2O_7$) was prepared and tested for mechanical strength and chemical stability, and demonstrates superior properties to calcium silicate for bioactivity and mechanical strength. Indeed, the mechanical strength of Sr-Hardystonite is higher than Sr—$CaSiO_3$ (see FIG. 2). Strontium doped Hardystonite has also been tested in vitro and in vivo and has been shown to be biocompatible and to support bone cell adherence and differentiation. For example, see FIG. 3 in which $Ca_2ZnSi_2O_7$ shows no apatite formation ability in SBF, but Sr—$Ca_2ZnSi_2O_7$ ($Sr_{0.1}Ca_{1.9}ZnSi_2O_7$) clearly demonstrates apatite-formation in SBF (see FIG. 7). The new material of the invention is considered especially useful for skeletal tissue regeneration.

Apatite-Formation Ability of Ceramics in Simulated Body Fluid (SBF)

SBF containing ion concentrations similar to those found in human blood plasma was prepared as previously described (Wu C, Ramaswamy Y, Kwik D, Zreiqat H. *The effect of strontium incorporation into CaSiO$_3$ ceramics on their physical and biological properties. Biomaterials* 2007; 28(21): 3171-81). Briefly, reagent-grade $CaCl_2$, $K_2HPO_4.3H_2O$, NaCl, KCl, $MgCl_2.6H_2O$, $NaHCO_3$, and $Na_2SO_4$ in appropriate amounts were dissolved in distilled water and pH adjusted to 7.4. Ceramic disks of HT and Sr-HT were soaked in SBF at 37 for 14 days, and the ratio of disc surface area to solution volume of SBF was 0.1 cm$^2$/ml. The soaked disks were dried at 100° C. for 1 day and characterized using scanning electron microscopy (SEM) coupled with energy dispersive spectrometer (EDS, Philips XL 30 CP, Netherlands).

Isolation and Culture of Primary HOB

HOB were isolated from normal human trabecular bone as previously described (Zreiqat H, Valenzuela S M, Nissan B B, Roest R, Knabe C, Radlanski R J, et al. *The effect of surface chemistry modification of titanium alloy on signalling pathways in human osteoblasts. Biomaterials* 2005; 26(36):7579-86). Briefly, bone was divided into 1 mm$^3$ pieces, washed several times in phosphate buffered saline (PBS), and digested for 90 min at 37° C. with 0.02% (w/v) trypsin (Sigma-Aldrich, USA) in PBS. Digested cells were cultured in complete media containing a-Minimal Essential Medium (α-MEM, Gibco Laboratories, USA), supplemented with 10% (v/v) heat-inactivated fetal calf serum (FCS, Gibco Laboratories, USA), 2 mM L-glutamine (Gibco Laboratories, USA), 25 mM Hepes Buffer (Gibco Laboratories, USA), 2 mM sodium pyruvate, 30 mg/ml penicillin, 100 mg/ml streptomycin (Gibco Laboratories, USA) and 0.1 M L-ascorbic acid phosphate magnesium salt (Wako Pure Chemicals, Osaka, Japan). The confluent cells were used to determine HOB attachment, proliferation, differentiation and their gene regulation.

Attachment of HOB

HOB seeded at cell density of 1.5×10$^4$ cells/cm$^2$ on Sr-HT scaffolds were allowed to attach for 3 days. At the end of each time point cells were fixed with 125% glutaraldehyde, 4% paraformaldehyde and 4% sucrose and post fixed in 1% osmium tetroxide followed by sequential dehydration in graded ethanol (70%, 90%, 95% and 100%), before drying in hexamethyldisilizane and coating with gold for SEM analysis.

Proliferation of HOB

HOB cell proliferation was quantitatively assessed by MTS (3-(4,5-dimethylthiazol-2-yl)-2,5-diphenyltetrazoliumbromide) assay after 1, 3 and 7 days of culturing $2.7 \times 10^4$ cells/cm$^2$ on Sr-HT, HT scaffolds and Tissue Culture Plastic (TCP) was used as an internal control for the tissue culture. Three scaffolds of each type were tested for each culture time and proliferation was evaluated using MTS assay. Hundred microliter of the reacted reagent from each well was transferred to 96-well plate and the absorbance was recorded using a microplate reader (PathTech, Australia) at 490 nm using the software Accent.

Figure 14:
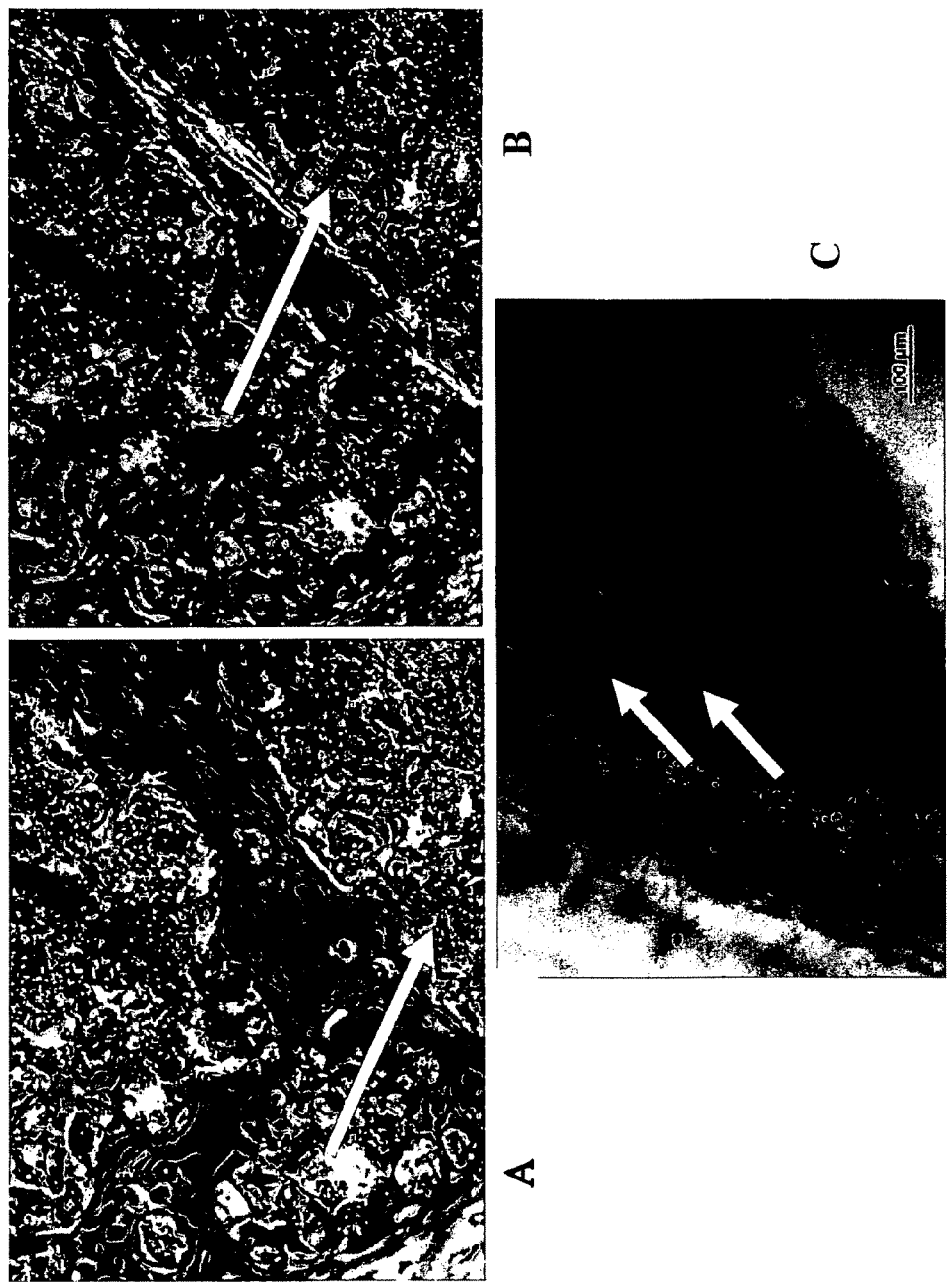
FIG. 14A shows high induction of bone formation in Sr-HT material, and using birefringence under polarized light illumination the collagen nature of this material is highlighted in FIG. 14B.
FIG. 14C shows histological staining of undecalcified sections of bone in contact with Sr-HT, which shows a substantial amount of alkaline phosphatase activity being stimulated (arrows) over the bone, which is particularly indicative of ongoing bone formation on existing bone surfaces, and therefore indicative of the materials osteoconductivity.

Ceramic Microspheres Subcutaneously Implanted in SCID Mice to Determine Osteoinductivity The biocompatibility of Sr-HT ceramics were determined by implanting microspheres of the material subcutaneously into the flanks of NOD/SCID mice for 8 weeks with human mesenchymal stem cells. The materials were well tolerated without excessive induction of fibrous tissue or evidence of inflammation post transplantation as shown in the representative Figure for Sr-HT (FIGS. 14A and 14B).

Ceramic Microspheres Implanted Over the Mouse Calvaria to Determine Osteoconductivity The biocompatibility of Sr-HT bioceramics was further confirmed by implanting microspheres of this material in the mice calvaria for 3 weeks. The Sr-HT material was well tolerated with significant induction of bone but without induction of fibrous tissue or evidence of inflammation following 3 weeks post transplantation (see FIG. 14C).

In Vivo Osteoconductivity of the Sr-HT 3-D Scaffold in a Rodent Bone Defect Model.

The osteoconductivity of the Sr-HT material was confirmed in a rodent bone defect model. The developed scaffolds Sr-HT, Sr—CaSiO$_3$, and the clinically relevant scaffold (β-TCP), were implanted in the cortical defect of rat tibia for 3 weeks (8 animals per group). Preliminary analysis indicates that at 3 weeks Sr-HT is osteoconductive and biocompatible and demonstrates close apposition with invading bone.

The results demonstrated herein show that Sr-HT scaffolds provide similar mechanical strength to cancellous bone, indicating their potential to support load bearing. The in vivo data demonstrates that Sr-HT scaffolds are not only bioactive (i.e. can support bonding with host bone), but are also biocompatible (i.e. no evidence of inflammation or fibrous tissue formation).

It has been surprisingly found that the addition of both Sr and Zn into a calcium silicate biomaterial provides properties to the resulting biomaterial which surpass the effects of previously known calcium silicate biomaterials. It has been found by the applicant that relatively reduced rates of calcium dissolution are apparent, and well as surprisingly improved mechanical, physical and chemical properties.

In conclusion, the strontium calcium zinc silicate of the present invention shows favourable bio-ceramic properties with increased bending strength and fracture toughness. It also shows improved biological properties. Without being bound by theory, it appears that the improved mechanical properties can be attributed to zinc whilst the strontium may contribute to improvement in biological properties. Thus the inclusion of both strontium and zinc in the calcium silicate framework appears to provide an additive effect.

Although the invention has been described with reference to specific examples, it will be appreciated by those skilled in the art that the invention may be embodied in many other forms. In particular features of any one of the various described examples may be provided in any combination in any of the other described examples.

The invention claimed is:

1. A biocompatible ceramic material having a molecular formula:

$$[(Sr_aBa_bMg_c)Ca_{[2.0-\Sigma(a,b,c)]}ZnSi_2O_7]$$

wherein $\Sigma(a,b,c)$ is between 0.05 to 0.9.

2. A biocompatible calcium zinc silicate ceramic material comprising the molecular formula $Sr_xCa_{(2-x)}ZnSi_2O_7$, 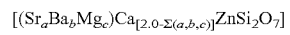 wherein x is between 0.05 to 0.9.

3. The biocompatible material according to claim 2 wherein x=0.1.

4. A biocompatible material comprising strontium calcium zinc silicate wherein said strontium calcium zinc silicate is strontium doped Hardystonite (Ca$_2$ZnSi$_2$O$_7$).

5. The biocompatible material according to claim 1 wherein said material is a medical grade or an implant grade material.

6. The biocompatible material according to claim 1 wherein said material comprises a purity of greater than about 99%.

7. A biocompatible material comprising strontium calcium zinc silicate comprising a transmission λ-ray diffraction pattern having the following diffraction angles at 2θ:
   line of strong intensity: 31.44 degrees,
   line of medium intensity: 29.225 degrees, and
   line of third strongest intensity: 36.565 degrees.

8. A biocompatible material comprising strontium calcium zinc silicate comprising a transmission X-ray diffraction pattern as per FIG. 1A.

9. The biocompatible material according to claim 1 wherein said material forms a hydroxyapatite layer upon exposure to bodily fluids.

10. The biocompatible ceramic material according to claim 1 which is synthetically prepared.

* * * * *